(12) United States Patent  
Schwarz et al.

(10) Patent No.: US 8,355,141 B2  
(45) Date of Patent: Jan. 15, 2013

(54) DEVICE FOR THE INVESTIGATION OF TEXTURED SURFACES

(75) Inventors: Peter Schwarz, Koenigsdorf (DE); Uwe Sperling, Geretsried (DE)

(73) Assignee: BYK-Gardner GmbH (DE)

( * ) Notice: Subject to any disclaimer, the term of this patent is extended or adjusted under 35 U.S.C. 154(b) by 272 days.

(21) Appl. No.: 12/833,709

(22) Filed: Jul. 9, 2010

(65) Prior Publication Data

US 2011/0013197 A1 Jan. 20, 2011

(30) Foreign Application Priority Data

Jul. 15, 2009 (DE) .......................... 10 2009 033 110

(51) Int. Cl.  
*G01B 11/24* (2006.01)

(52) U.S. Cl. ....................................... 356/600; 356/601

(58) Field of Classification Search ........... 356/600–614  
See application file for complete search history.

(56) References Cited

U.S. PATENT DOCUMENTS

| | | | | |
|---|---|---|---|---|
| 5,155,558 | A | * | 10/1992 | Tannenbaum et al. ........ 356/446 |
| 2005/0128484 | A1 | * | 6/2005 | Rodrigues et al. ............ 356/402 |
| 2007/0206195 | A1 | * | 9/2007 | Sperling ........................ 356/446 |
| 2009/0046300 | A1 | * | 2/2009 | Schwarz et al. ............... 356/600 |

* cited by examiner

*Primary Examiner* — Michael P Stafira  
(74) *Attorney, Agent, or Firm* — Hayes Soloway P.C.

(57) ABSTRACT

A method for optical investigation of textured surfaces involves the steps of irradiation of radiation onto the surface to be investigated; reception of an image from at least part of the radiation irradiated onto the surface and reflected by the surface; location-resolved evaluation of the image recorded and determination of at least one value K which is characteristic of this image. A parameter G which is characteristic of the surface is determined while using the characteristic value K and while using at least one further property E known beforehand or determined of the surface.

25 Claims, 1 Drawing Sheet

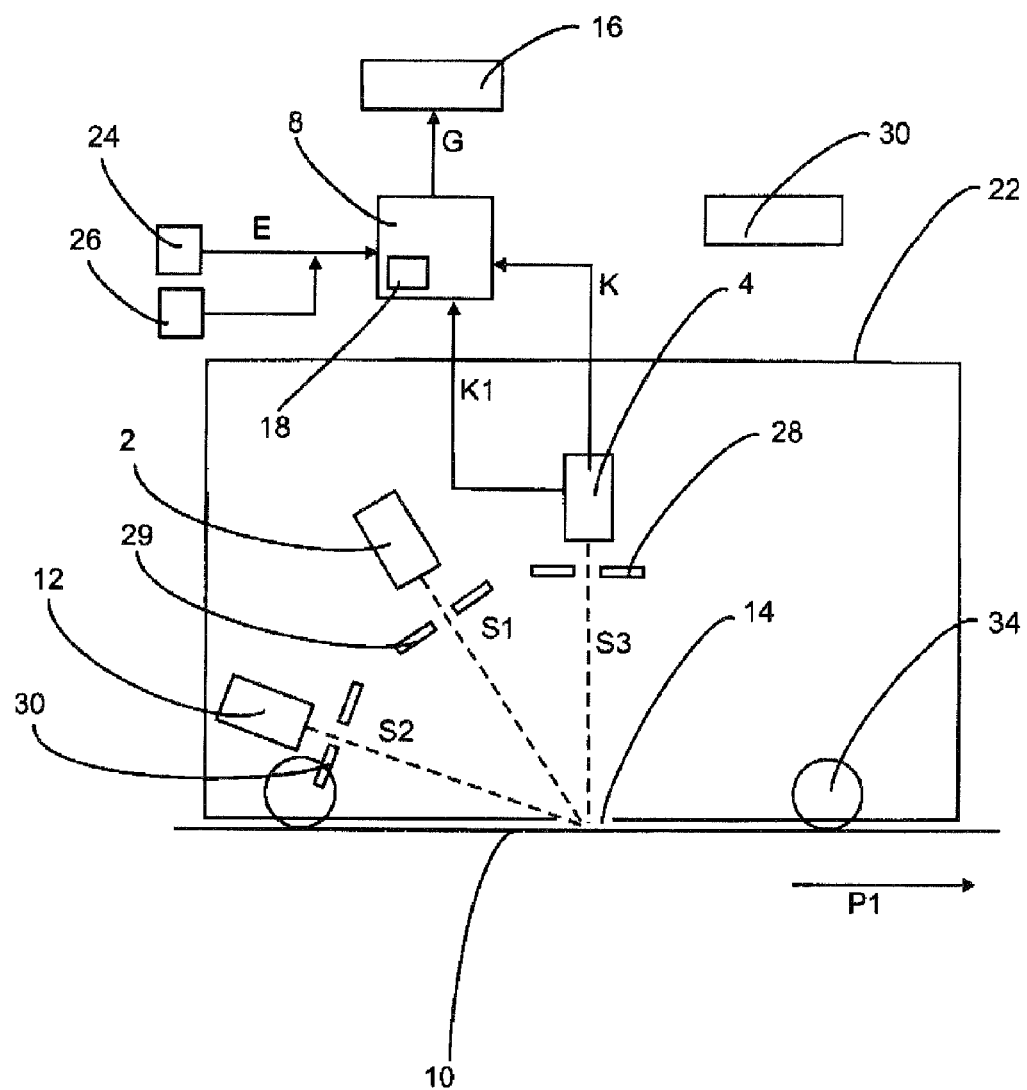

DEVICE FOR THE INVESTIGATION OF TEXTURED SURFACES

BACKGROUND OF THE INVENTION

The present invention relates to a method and a device for the investigation of textured surfaces. In this case the present invention is described with reference to the surfaces of vehicle bodies, but it is also stated that the device is also applicable to other surfaces such as for example the surface of floors or pieces of furniture. Textured surfaces are to be understood as being those surfaces which are not completely flat but rather have (regular or even statistically distributed) uneven portions or differences in height. The textured surface is thus characterized by a topography which as well as a lateral extension also [has] a vertical profile. The human eye, however, cannot evaluate such differences in height quantitatively in the micrometer range but only observes the effects of this texture.

Various devices and methods which detect unevenness of this type are known from the prior art. In this way, for example, so-called Hommel instruments are known which measure the uneven portions themselves. These devices are relatively complicated, however, and always require a mechanical contact with the surface to be investigated. In addition, other types of surface-measuring instruments are known, which, however, likewise measure the surface itself physically (in particular by sensing).

Furthermore, devices and methods of investigating surfaces are known from the prior art, which measure this surface optically in order to investigate parameters such as for example the colour, the brightness or the DOI (distinctiveness of image). Instruments of this type are used in particular in the range of quality assurance, in particular when differences are to be determined between two surfaces to be compared. In this case too, however, it is not so much the quantitatively existing difference which is decisive but rather the human perception.

The problem arises in this case that the results of these investigations are not always unambiguous. Furthermore, in the final analysis, instruments of this type are used to investigate surfaces in order to establish as objective as possible a picture of the surface as it also appears to an observer.

In this case the phenomenon occurs that during the optical detection of objects the brain of the human observer usually draws upon experiences which then allow the observer to evaluate surfaces in a precise manner. In this way, the human observer can estimate, by observation on the basis of his or her experience, the materials of which specific surfaces can consist.

The object of the present invention is therefore to make available a method and a device which permit an objective evaluation of a surface, in particular a textured surface, without a mechanical measurement of this surface having to be carried out.

SUMMARY OF THE INVENTION

In a method according to the invention for the optical investigation of textured surfaces, in one method step radiation is irradiated onto the surface to be investigated. In a further method step, an image is received from at least part of the radiation irradiated onto the surface and reflected by the surface, and in a further step a location-resolved evaluation of the image recorded is carried out and at least one value which is characteristic of this image is determined.

According to the invention a magnitude which is characteristic of the surface is investigated whilst using the characteristic value and whilst using at least one property—known beforehand or determined—of the surface. The value which is characteristic of the image can be for example brightness values or colour values of the individual pixels. This characteristic value can also be a statistical characteristic value, such as for example a variance. In addition, the characteristic value can also be formed from a plurality of individual values, for example in the form of an array.

The parameter which is characteristic of the surface can be a parameter which is characteristic of the texture of this surface, in which case too it can also be a qualitative value which can provide a comparison for reference purposes.

In this way for example the characteristic parameter can be a value which indicates whether the surface to be investigated is still within a tolerance range with respect to the reference surface. This is important for example in the case of vehicles when bodywork parts or parts of the vehicle interior have to be replaced and it has to be established by measurement methods whether the optical impressions of these bodywork parts to be replaced will be perceived by an observer as being optically identical or already different.

The use of the at least one further property—known beforehand or determined—of the surface takes into consideration the fact that in practice the user would likewise (at least unconsciously) draw upon values from experience. In this way, for example, an image supplied by an image-recording device such as for example a colour or a grey-scale camera could have a multiplicity of brighter and darker points. These brighter and darker points could have a number of causes, however, for example they could result from multi-coloured portions of this surface or even from effect pigments and or they could also derive from single-colour textured surfaces.

If the device has been given the information beforehand that textured surfaces, for example even with a specific colour, are being measured, then on the basis of the previously known property a realistic assessment of the evaluated image of the camera is possible. In this way within the scope of the invention it is proposed for the first time that the mode of operation of the human brain is simulated, which also evaluates its colour impressions on the basis of experience. It would also be possible, however, for no previously known property to be used, but for a plurality of measurements to be carried out. It would also be possible, however, for further parameters to be used as a previously known property.

The surface could thus be recorded from a plurality of sides. In this way it is likewise possible to check for example whether a specific image derives from a multi-colour surface or, on the other hand, from a textured surface. It is preferable for the parameter which is characteristic of the surface to be determined without the textured surface being measured.

This means that the characteristic parameter is not directly determined by the fact that the surface is measured mechanically for example by a Hommel instrument or even by layer-thickness measurement or the like, but indirectly by means of the optical investigation claimed according to the invention. In particular, it is preferable if differences in the height of the surface in question are also not measured, but only an image is preferably evaluated whilst using values from experience.

In a further advantageous method, results of the evaluation of the recorded image are compared with reference data. In this way, in order to evaluate the image, it would be possible for example for a specified characteristic value, for example a statistical characteristic value, to be formed and for the latter to be compared with a reference value. A result of this comparison can be transmitted to the user, for example a statement as to whether a specified surface is capable of being differentiated optically by the user with respect to the reference surface.

In a further advantageous method a qualitative investigation of the surface is carried out. This means that no precise quantitative details on the surface are given, but they are compared only qualitatively with a reference and the conclusions are drawn just from this qualitative comparison.

In a further advantageous method at least the irradiation and/or the recording of the image is or are carried out from at least two different angles. In this way it would be possible for two radiation sources to irradiate the light onto the surface at two different angles and for the image-recording device to record—preferably with a time delay—the light irradiated from the two light sources. As a result of this illumination at different angles, two different measurements are likewise available and conclusions on the texture of the surface can be drawn from their results. It is likewise possible, however, for only one light source and for two image-recording devices for said light source to be used in order to make a number of angles possible in this way. In this case the light source could be activated twice for the two different measurements. It would also be possible for a plurality of light sources and a plurality of image-recording devices to be provided.

In a further advantageous method standard light is used to irradiate the surface. It is preferable to use a light source which makes available a so-called D65 illumination.

In a further advantageous method the further property of the surface is selected from a group of properties, which contains a material of the surface, a reflectivity of the surface, colour properties of the surface, texture properties of the surface, brightness contrasts of the surface, combinations thereof or the like. This further property takes into consideration the experience of a human observer who is gaining his or her optical impressions of a surface just on the basis of this experience.

In a further advantageous method diffuse or non-directed radiation is irradiated onto the surface. In another method a directed radiation could also be used, depending upon what type of natural light is to be simulated.

It is advantageous for the characteristic value to be a statistical magnitude. It can be for example a normal distribution, arithmetical or geometrical averages, variances, entropy, fractal elements, or a co-occurrence matrix or other mathematical methods of evaluating one- or two-dimensional images.

It is preferable for the characteristic value to be determined from an evaluation of a multiplicity of individual values of the location-resolved image. In this way, for example, a plurality of pixel values could be used which represent different stages of brightness.

The radiation can be both diffuse and directed radiation, in which case these two types of radiation can also be combined during a measurement process. In addition, it is also possible for multilateral illumination to be carried out, for example from annular-segmental light sources. Furthermore, it would be possible to use convergent or divergent radiation or optionally to use a so-called Ulbricht sphere.

In a further advantageous method an image-evaluation method of the human eye is simulated.

The present invention further relates to a device for the optical investigation of textured surfaces, which has at least one radiation device which irradiates radiation at a pre-determined angle to the surface to be investigated and has at least one image-recording device which records at least part of the radiation irradiated onto the surface by the radiation device and reflected by the surface. In this case the image-recording device is suitable for recording a location-resolved image and, in addition, a processor device is provided which determines at least one value which is characteristic of this image.

According to the invention the processing device is designed in such a way that it determines a value which is characteristic of the surface whilst using the characteristic value and whilst using at least one further property—known beforehand or determined—of the surface. The image-recording device is advantageously a colour-image camera or a black-and-white-image camera.

This means that the processor device according to the invention also not only delivers a result on the basis of the image data but, as well as this, uses the above-mentioned additional property. It would also be possible however, for this previously known property to be the result of a further measurement which is carried out on the surface. In this case this further measurement is advantageously carried out in the same region of the surface as the measurement to be evaluated. It is advantageous for the device to have a memory device for storing at least one characteristic value or a value which is characteristic of the property which is known beforehand or determined.

Furthermore, it is advantageous if at least one characteristic value and preferably a plurality of characteristic values for the surface to be investigated is or are stored in the memory device. The characteristic values can be values which describe optical properties of the surface, such as for example colour properties or the like.

In a further advantageous embodiment the device has at least one further radiation device or at least one further image-recording device. In this case it is advantageous for the radiation device and the image-recording device to be provided in a housing, this housing preferably having an opening for illuminating the surface to be investigated and is advantageously otherwise closed.

In a further advantageous embodiment the image-recording device is arranged at an angle of 90° with respect to the surface.

In a further advantageous embodiment the device has a comparator which compares at least one detected characteristic value with a reference value. The FIGURE emitted by the device is advantageously a relative magnitude, such as a difference or a ratio, but it is also possible for weighted coefficients to be used.

BRIEF SUMMARY OF THE DRAWINGS

Further advantageous embodiments are illustrated in the attached drawing, in which FIG. 1 shows a device according to the invention for the investigation of a surface.

DETAILED DESCRIPTION

FIG. 1 shows a device 1 according to the invention for the investigation of a surface 10. In this case this surface 10 is, in particular, textured, i.e. in particular it is not made flat. The reference number 22 designates a housing, in the interior of which a first radiation device 2 and an image-recording device 4 are arranged. In this case the housing 22 is designed in a light-tight manner and has only one opening 14 through which the surface 10 can be illuminated and an image of the surface can be recorded. The radiation device 2 illuminates the surface 10 (cf. beam S2).

The radiation reflected or scattered by the surface 10 is recorded by the image-recording device 4, i.e. the image-recording device 4 records an image of the illuminated surface 10. The housing is preferably made light-absorbing in its interior, so that the measurements are not be falsified by extraneous reflexes. Depending upon the measurement to be carried out, however, the internal surface of the housing could also be made reflecting, so that the internal surface of the housing forms a so-called Ulbricht sphere.

In this case the radiation device 2 can have one or more light-emitting diodes as a light source. In this way, white-light LEDs could be used, but it would also be possible for a plurality of LEDs of different colour to be used, in order to keep the colour properties of the irradiated light variable or to produce standard light, such as for example D65 light. In addition, other light sources such as halogen lamps, xenon (flash) lamps, incandescent lamps, lasers or the like could be used for illumination purposes.

Furthermore, refractive elements (not shown) such as lenses or the like or even screens could be provided in the light path between the light source and the surface 10.

The corresponding image data k delivered by the image-recording device are passed on to a processor device designated 8 in its entirety. In this case these data K represent only the image recorded by the image-recording device 4 or a colour image or grey-scale image. The processor device 8 in turn evaluates this recorded image, in which case the processor device 8 uses further data E for this purpose. These further data E are not derived, in particular, from the specific measurement from which the data K are derived. In this way, the data E are independent of the data K and, in particular, are also obtained independently of them.

In this way, it would be possible for example for the further data E to be derived from a memory device 24 in which previously known characteristic data of the surface 10 are stored, for example data on the colour and the material of the surface. Furthermore, a memory device 26 can also be provided in which earlier data of the above-mentioned surface are stored or even reference data of a corresponding reference surface or data recorded in another region of the surface and/or at a different time and/or at a different angle.

The reference number 18 designates a comparator which compares the characteristic values detected with stored reference values and delivers results of this comparison.

The processor device 8 takes into consideration said data E and delivers a result value G to a display device 16. These result data G can be for example a purely qualitative value which gives information as to whether the investigating surface is within a specified standard range.

The reference number 12 designates a further radiation device which is arranged at a further angle with respect to the surface 10 and irradiates light onto the surface along the radiation direction S2. It would thus also be possible to obtain the corresponding qualitative image of the surface by two measurements, one measurement being obtained by illumination with the radiation device 2 and a further measurement being obtained by illumination with the radiation device 12. It is advantageous for these two radiation directions S1 and S2 and the radiation direction S3, which extends from the surface 10 in the direction of the image-recording device 4, to be situated in one plane. It would also be possible, however, for the detectors or radiation sources for example to be arranged outside the measurement plane.

The radiation devices 2 and 12 preferably emit standardized light such as for example D65 light. In this case it is possible for the two radiation devices to be activated simultaneously, but a successive activation would also be possible. It would be possible that the radiation devices are capable in each case of transmitting light of different colours onto the surfaces. Furthermore, screens and filter devices 28 can also be arranged in the radiation paths S1, S2 and S3 respectively, in order to investigate the surface. The reference numbers 29 and 30 designate further screens and/or filter devices which are arranged in the respective radiation paths between the radiation devices 2 and 12 and the surface.

The radiation sources can be operated in a continuous mode, but a pulsed or chopped operation would also be possible. This pulsed operation allows the ambient light to be compensated. In this case this compensation can be achieved by a comparison between an image, which was recorded only in ambient light, and a further image, which was recorded with illumination (overlaid by this ambient light).

Furthermore, it is possible for the entire arrangement, which is formed by the radiation device, the filters and the radiation-detector device, to be adapted spectrally in such a way that it obeys a pre-determined spectral sensitivity distribution, such as for example the $V_\lambda$ curve.

In this case the individual processor devices and memory devices 24, 26 and 8 are, in contrast to what is shown in FIG. 1, not arranged outside the housing 22 but preferably inside the housing or in a portion of the electronics provided for this. The afore-mentioned screens can be used to determine shine effects of the surface. It would also be possible, however, for the screens to be produced by the image evaluation, i.e. as "software screens" in which only limited areas of an image are evaluated.

The reference number 30 designates a control device in order to control for example the radiation devices 2 and 12 and optionally also the image-recording device. In this way it would be possible for the surface to be illuminated in succession by the two radiation devices S1 and S2 in the framework of a specified measurement mode and then for the two images to be evaluated by the processor device 12.

The reference number 34 designates a rolling device or a wheel which permits movement of the device 1 with respect to the surface along the arrow P1. The reference sign K1 designates further values which are delivered by the image-recording devices and which can also be used instead of or in addition to the value E in order to evaluate the image.

In addition, the device 1 has a distance-measuring device (not shown) which determines paths which the device covers with respect to the surface 10. In this way, the surface can be measured with a geometrical correlation in each case. A distance-measuring device of this type could be coupled to the wheels 34. It would also be possible, however, for the device 1 to be arranged on a stand and, in this way, to be moved with respect to the surface 10 in a defined manner.

All the features disclosed in the application documents are claimed as being essential to the invention, insofar as they are novel either individually or in combination as compared with the prior art.

LIST OF REFERENCES 1 device
2 radiation device
4 image-recording device, detector device
8 processor device
10 surface
14 opening
16 display device
18 comparator
22 housing
24 memory device
26 memory device
28 screen
30 control device 34 wheel
S1, S2, S3 directions

The invention claimed is:

1. A method for the optical investigation of textured surfaces comprising the steps of:
   irradiation of radiation onto the surface to be investigated;
   reception of an image from at least part of the radiation irradiated onto the surface and reflected by the surface; and
   location-resolved evaluation of the image recorded and determination of at least one value (K) which is characteristic of said image,
   wherein a parameter (G) which is characteristic of the surface is determined whilst using the characteristic value (K) and whilst using at least one further property (E)—known beforehand or determined—of the surface, wherein the parameter which is characteristic of the surface is determined without textured surface being measured.

2. The method according to claim 1, wherein the parameter which is characteristic of the surface is determined without the textured surface being measured and without a vertical profile of the surface being measured.

3. The method according to claim 1, wherein results of the evaluation of the recorded image are compared with reference data.

4. The method according to claim 1, wherein a qualitative investigation of the surface is carried out.

5. The method according to claim 1, wherein at least the irradiation of the radiation and/or the recording of the image is or carried out from at least two different angles.

6. The method according to claim 1, wherein standard light is used to irradiate the surface.

7. The method according to claim 1, wherein the further property of the surface is selected from a group of properties, which contains a material of the surface, a reflectivity of the surface, colour properties of the surface, texture properties of the surface, brightness contrasts of the surface, and combinations thereof.

8. The method according to claim 1, wherein diffuse radiation is irradiated onto the surface.

9. The method according to claim 1, wherein the characteristic value (K) is a statistical magnitude.

10. The method according to claim 1, wherein the characteristic value is determined from an evaluation of a multiplicity of individual values of the location-resolved image.

11. The method according to claim 1, wherein pulsed radiation is used.

12. The method according to claim 1, wherein an image-evaluation method of the human eye is simulated.

13. A device for the optical investigation of textured surfaces with at least one radiation device which irradiates radiation at a pre-determined angle onto the surface to be investigated, with at least one image-recording device which records at least part of the radiation irradiated onto the surface by the radiation device and reflected by the surface, wherein the image-recording device is suitable for recording a location-resolved image, and with a processor device which determines at least one value which is characteristic of this image, wherein the processor device is designed in such a way that it determines a parameter which is characteristic of the surface whilst using the characteristic value (K) and whilst using at least one further property (E) which is known beforehand or determined—of the surface, and wherein the processor device is designed in such a way that it determines the parameter which is characteristic of the surface without the textured surface being measured.

14. The device according to claim 13, wherein the device has a memory device for storing at least one characteristic value or a value which is characteristic of the property—known beforehand or determined.

15. The device according to claim 13, wherein the device has at least one further radiation device or at least one further image-recording device.

16. The device according to claim 13, wherein the image-recording device is arranged at an angle of 90° with respect to the surface.

17. The device according to claim 13, wherein the device has a comparator which compares at least one detected characteristic value with a reference value.

18. The method according to claim 2, wherein at least the irradiation of the radiation and/or the recording of the image is or carried out from at least two different angles.

19. The method according to claim 3, wherein at least the irradiation of the radiation and/or the recording of the image is or carried out from at least two different angles.

20. The method according to claim 4, wherein at least the irradiation of the radiation and/or the recording of the image is or carried out from at least two different angles.

21. The method according to claim 1, wherein the characteristic parameter is a value which indicates whether the surface to be investigated is still within a tolerance range with respect to the reference surface.

22. A method for the optical investigation of textured surfaces comprising the steps of:
   irradiation of radiation onto the surface to be investigated;
   reception of an image from at least part of the radiation irradiated onto the surface and reflected by the surface; and
   location-resolved evaluation of the image recorded and determination of at least one value (K) which is characteristic of this image,
   wherein a parameter (G) which is characteristic of the surface is determined whilst using the characteristic value (K) and whilst using at least one further property (E)—known beforehand or determined—of the surface, and wherein the data E are independent of the data K and are also obtained independently of them.

23. A device for the optical investigation of textured surfaces with at least one radiation device which irradiates radiation at a pre-determined angle onto the surface to be investigated, with at least one image-recording device which records at least part of the radiation irradiated onto the surface by the radiation device, and reflected by the surface, wherein the image-recording device is suitable for recording a location-resolved image, and with a processor device which determines at least one value which is characteristic of this image, wherein the processor device is designed in such a way that it determines a parameter which is characteristic of the surface whilst using the characteristic of the surface whilst using the characteristic value (K) and whilst using at least one further property (E) which is known beforehand or determined—of the surface, and wherein the data E are independent of the data K and wherein the processor device is designed in such a way that it also obtains data E independently of data K.

24. The method according to claim 1, wherein differences in the height of the surface in question are not measured, but only an image is evaluated whilst using values from experience.

25. The method according to claim 1, wherein the characteristic parameter is not directly determined by the fact that the surface is measured mechanically.

* * * * *